(12) United States Patent
Krishnamurthy et al.

(10) Patent No.: US 10,144,703 B2
(45) Date of Patent: Dec. 4, 2018

(54) PROCESS FOR THE PREPARATION OF VERAPAMIL HYDROCHLORIDE

(71) Applicant: PIRAMAL ENTERPRISES LIMITED, Mumbai (IN)

(72) Inventors: Dhileep Kumar Krishnamurthy, Maharashtra (IN); Milind Gharpure, Maharashtra (IN); Narender Rao Somisetti, Telengana State (IN); Murali Rajappa, Telengana State (IN); Rajshekar Aareddy, Telengana State (IN); Damodhar Kasireddy, Telengana State (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

(21) Appl. No.: 15/570,821

(22) PCT Filed: May 10, 2016

(86) PCT No.: PCT/IB2016/052648
§ 371 (c)(1),
(2) Date: Oct. 31, 2017

(87) PCT Pub. No.: WO2016/181292
PCT Pub. Date: Nov. 17, 2016

(65) Prior Publication Data
US 2018/0127354 A1    May 10, 2018

(30) Foreign Application Priority Data
May 12, 2015  (IN) .................... 1864/MUM/2015

(51) Int. Cl.
C07C 253/30    (2006.01)
C07C 213/08    (2006.01)
C07C 217/60    (2006.01)
C07C 255/42    (2006.01)
B01J 31/02     (2006.01)
C07B 63/00     (2006.01)

(52) U.S. Cl.
CPC ......... *C07C 253/30* (2013.01); *B01J 31/0239* (2013.01); *C07B 63/00* (2013.01); *C07C 213/08* (2013.01); *C07C 217/60* (2013.01); *C07C 255/42* (2013.01); *C07C 2531/02* (2013.01)

(58) Field of Classification Search
CPC ... C07C 213/08; C07C 217/60; C07C 253/30; C07C 255/42
See application file for complete search history.

(56) References Cited

U.S. PATENT DOCUMENTS 3,261,859 A    7/1966  Dengel et al.
4,418,017 A    11/1983 Seitz et al.
2009/0171110 A1  7/2009 Albani et al.

FOREIGN PATENT DOCUMENTS

DE    2 059 923 A    6/1972

OTHER PUBLICATIONS

Johnston, et al.; Systemic availability of oral verapamil and effect on PR interval in man; Br. J. Clin. Pharmac. (1981), 12, 397-400).

*Primary Examiner* — Valerie Rodriguez-Garcia
(74) *Attorney, Agent, or Firm* — Ladas & Parry LLP

(57) ABSTRACT

A process for the preparation of 5-(3,4-dimethoxyphenyl-ethyl) methyl-amino-2-(3,4-dimethoxyphenyl)-2-isopropyl valeronitrile, which is known as Verapamil is described. A process for improving the purity of verapamil and therefore of its hydrochloride represented as the compound of formula I, by efficient removal of the impurities formed, affording a product of purity greater than 99% is described.

15 Claims, No Drawings

PROCESS FOR THE PREPARATION OF VERAPAMIL HYDROCHLORIDE

RELATED APPLICATION

This application is a national phase entry under 35 USC 371 of International Patent Application No.: PCT/IB2016/052648 filed on 10 May 2016, which claims priority from Indian Application No. 1864/MUM2015 filed on 12 May 2015, the disclosures of which are incorporated in their entirety by reference herein.

FIELD OF THE INVENTION

The present invention relates to a process for the preparation of 5-(3,4-dimethoxyphenylethyl) methyl-amino-2-(3,4-dimethoxyphenyl)-2-isopropyl valeronitrile, which is known as Verapamil and the hydrochloride salt thereof. The present invention also relates to a process for improving the purity of verapamil hydrochloride by efficient removal of the impurities formed.

BACKGROUND OF THE INVENTION

Verapamil, or 5-(3,4-dimethoxyphenylethyl)methyl-amino-2-(3,4-dimethoxyphenyl)-2-isopropyl valeronitrile has been known for more than 20 years and its synthesis is described in Belgian Pat. No. 615 816 corresponding to the Dengel U.S. Pat. No. 3,261,859.

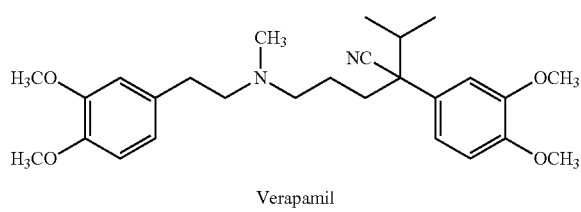 [SMILES: COc1ccc(CCN(C)CCCC(C#N)(c2ccc(OC)c(OC)c2)C(C)C)cc1OC]

Verapamil

The hydrochloride of verapamil is used in medicine for its remarkable antagonistic properties against intracellular penetration of calcium. It is an important drug for the treatment of angina pectoris when the attack is associated with a coronary spasm and beta-adrenolytic products such as propanolol, timolol, atenolol and pindolol are liable to have undesirable effects. It is also useful in the treatment of hypertension and cardiac arrythmia. It is known to the man of the art that the pharmacological action of verapamil is proportional to its concentration in the plasma (Br. J. Clin. Pharmac. (1981), 12, 397-400) and that the optimum therapeutic range extends from 100 ng/ml to 400 ng/ml of plasma.

Verapamil is presently in clinical use as the racemate and is used extensively for the treatment of hypertension. The opposite enantiomers of verapamil have different biological activities. The (S)-enantiomer (levoverapamil) has the majority of the calcium channel antagonist activity (DE-A-2059923) whilst the (R)-enantiomer (dextroverapamil) differs in having sodium channel and other cell-pump actions in addition to higher bioavailability, with slower clearance rate. Verapamil is a known Ca channel blocker and is a competitive inhibitor of P-glycoprotein. Processes for the preparation of verapamil are disclosed in several prior art documents such as U.S. Pat. No. 3,261,859 and U.S. Pat. No. 4,418,017. Verapamil obtained according to the procedure disclosed in these prior art documents involves the formation of a dimer along with various O-desmethyl and N-desmethyl derivatives of verapamil as impurities, which reduces the purity of verapamil and also lowers the yield due to repeated purification by multiple and elaborate crystallization processes.

The yield is reduced during the process of repeated purification. Therefore a need was felt to develop an efficient process of preparation of verapamil and further its hydrochloride, wherein the impurities formed during the process can be easily separated out without the requirement for repeated crystallization of the final product, thereby making the process of the present invention simple, efficient, cost-effective and industrially feasible.

The object of this invention is to provide an alternative process for the preparation of verapamil hydrochloride, the compound represented by Formula I herein, which process of the present invention will allow efficient large-scale synthesis by overcoming the drawbacks of the conventional technique involving formation of impurities.

OBJECTS OF THE INVENTION

An object of the present invention is to provide a process for the preparation of verapamil hydrochloride represented by formula I, which improves upon the limitations of the prior art process.

An object of the present invention is to provide a process for the preparation of verapamil hydrochloride by selective crystallisation, which enables effective removal of impurities formed, affording a product of higher purity.

An object of the present invention is to provide a process for the preparation of verapamil hydrochloride, with purity greater than 99%.

Still another object of the present invention is to provide a process for the preparation of verapamil hydrochloride which is simple, efficient, cost-effective and industrially feasible.

SUMMARY OF THE INVENTION

In accordance with an aspect of the present invention, there is provided a process for the preparation of verapamil hydrochloride represented by formula I comprising the steps of:

(a) reacting compound of formula II with chlorobromopropane using a base and a phase transfer catalyst in the presence of a solvent to yield compound of formula III;

(b) reacting the compound of formula III, obtained in step (a) with the compound of formula IV in the presence of a base and a solvent followed by reaction with an acetylating agent to yield compound of formula V; and (c) reacting the compound of formula V with hydrochloric acid in isopropyl alcohol to prepare the hydrochloride salt of verapamil, represented by the compound of formula I.

In accordance with another aspect of the present invention, the compound of formula V and therefore the compound of formula I is obtained with a purity greater than 99%, free of impurities constituted by a dimer. O-desmethyl and N-desmethyl verapamil derivatives.

The process of the present invention is depicted in the following scheme:

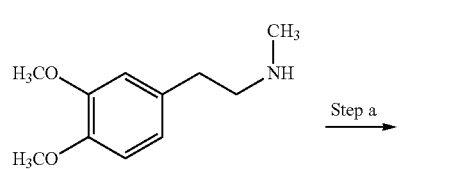

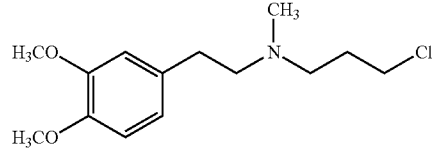

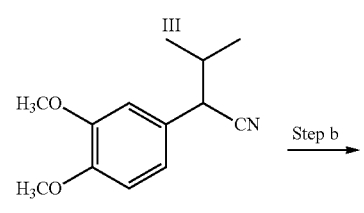

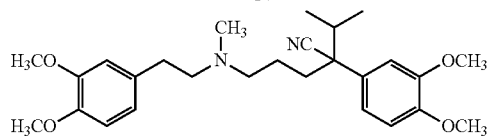

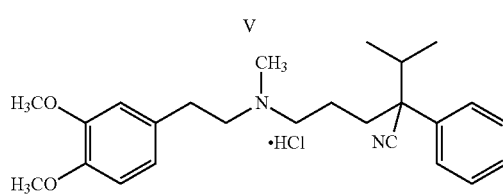

In accordance with yet another aspect of the present invention, the process employs non hazardous, environmentally friendly reagents, reduces cost, and increases purity and yield of the product.

DETAILED DESCRIPTION OF THE INVENTION

The present invention relates to a process for the preparation of verapamil hydrochloride represented as a compound of formula I,

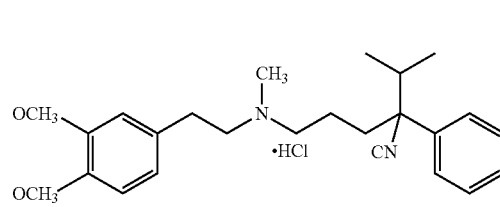

comprising the steps of:
a) reacting compound of formula II

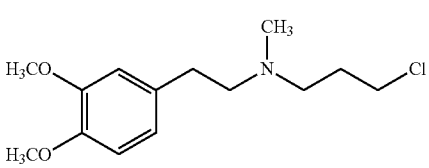

with chlorobromopropane, using a phase transfer catalyst in the presence of a base and a solvent to yield compound of formula III,

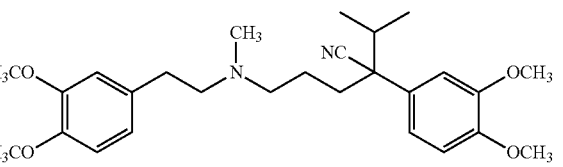

b) reacting the compound of formula III, obtained in step (a) with the compound of formula IV,

IV

H₃CO

H₃CO

CN in the presence of a base and a solvent, followed by reaction with an acetylating agent to yield the compound of formula V.

V

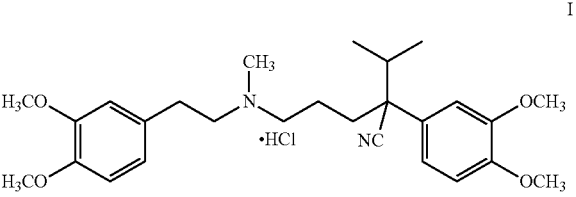

c) reacting the compound of formula V, obtained in step (b) using hydrochloric acid in isopropyl alcohol to prepare the corresponding hydrochloride salt represented as the compound of formula I.

I

Phenolic OH group can be protected with various protecting groups like acid chlorides and acid anhydrides. Once the —OH group is protected, the compound polarity as well as solubility will be changed. Among the —OH protecting groups, acetyl group is the simplest group and acetylation can be done using acetic anhydride which is commercially available low cost material. In Verapamil crude preparation, the organic layer, in particular the toluene layer containing Verapamil base is distilled off and co-distilled with isopropyl alcohol (IPA). Verapamil HCl salt is prepared by adding hydrochloric acid in isopropyl alcohol (IPA.HCl) to the IPA solution containing Verapamil base. It was thought that if the toluene layer is treated with acetic anhydride so that the desmethyl impurities (for example, the O-desmethyl derivative of verapamil obtained as impurity at 0.68 relative retention time (RRT)) are acetylated, on formation of the HCl salt of verapamil, the acetylated derivatives of the desmethyl impurities will also form the corresponding HCl salt. Further due to variation in solubilities of the HCl salts, the HCl salt of the acetylated derivatives of desmethyl impurities will be washed out during the selective HCl salt crystallization of verapamil.

The reaction involving the formation of desmethyl impurity at 0.68 RRT is provided herein.

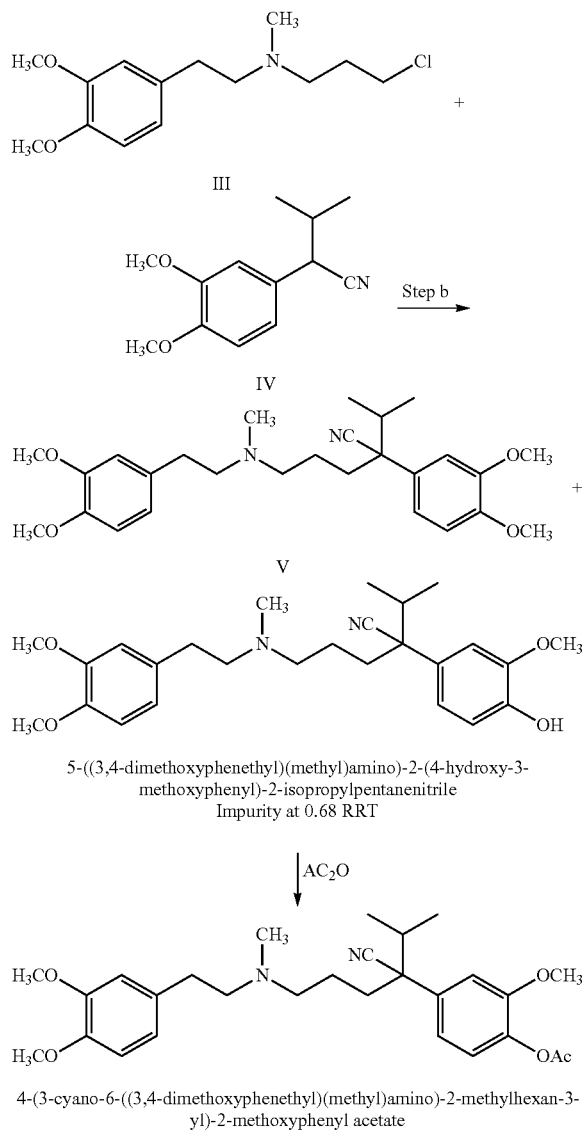

The present invention therefore relates to a process, which has the advantage of removing all the desmethyl impurities formed/carried over in the Verapamil base stage. The structures of the possible desmethyl verapamil derivatives obtained as impurities are as provided below.

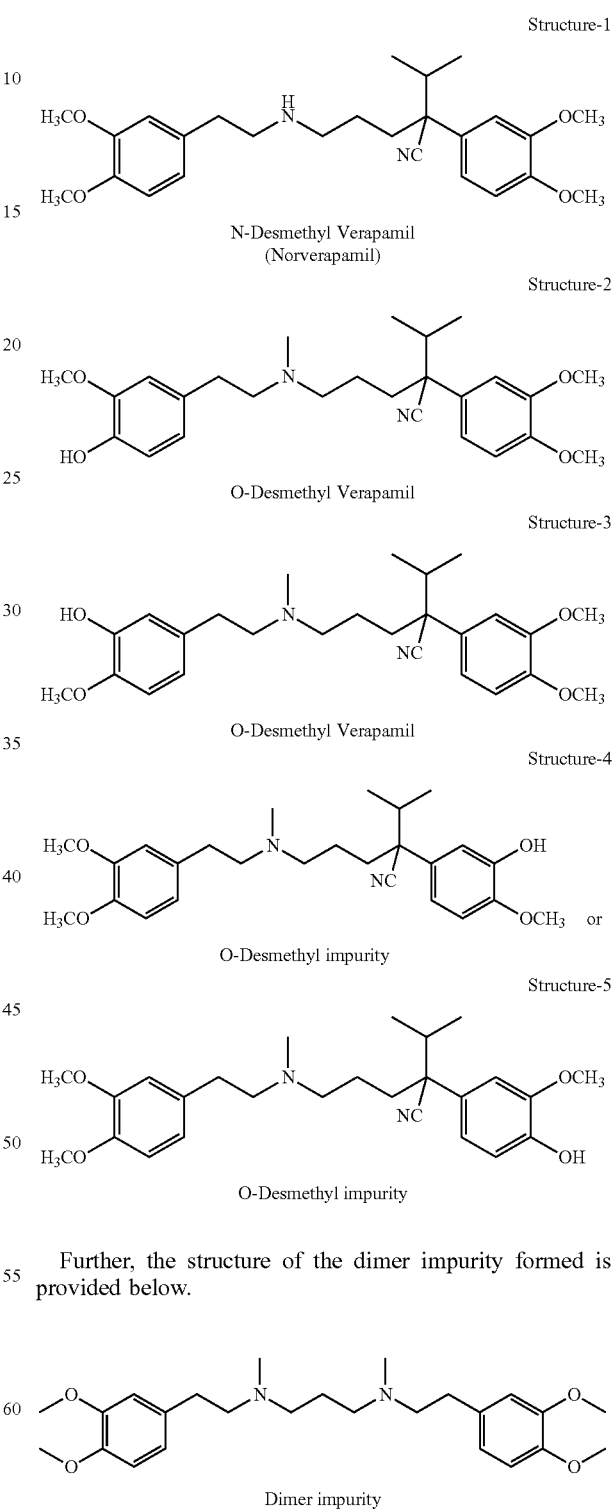

Further, the structure of the dimer impurity formed is provided below.

In accordance with an embodiment of the present invention, the phase transfer catalyst used in step (a) of the process for preparation of compound of formula III from compound of formula II is a quaternary ammonium salt.

In accordance with an embodiment of the present invention, the phase transfer catalyst used in step (a) of the process for preparation of compound of formula III from compound of formula II is a quaternary ammonium salt selected from the group consisting of ammonium salts such as tricaprylylmethylammonium chloride (Aliquat 336), tetra-n-butylammonium bromide, benzyltriethylammonium chloride (TEBA), cetyltrimethylammonium bromide, cetylpyridinium bromide. N-benzylquininium chloride, tetra-n-butylammonium chloride, tetrabutylammonium bromide (TBAB), tetra-n-butylammonium hydroxide, tetra-n-butylammonium iodide, tetraethylammonium chloride, benzyltributyl ammonium chloride, hexadecyltrimethylammonium chloride, tetramethylammonium chloride, hexadecyltrimethylammonium chloride, octyltrimethylammonium chloride or combinations thereof. In particular in case a combination of phase transfer catalysts are used, then one of the catalysts used in combination is preferably tetra butyl ammonium bromide (TBAB).

In accordance with an embodiment of the present invention, the phase transfer catalyst used in step (a) is tetrabutylammonium bromide (TBAB).

In accordance with an embodiment of the present invention, in the step (a) of the process, the next step for preparation of verapamil as free base is carried out directly without isolation of the product of step (a).

In accordance with an embodiment of the present invention, the said base used in step (a) is an inorganic base selected from the group consisting of sodium hydroxide, potassium hydroxide, lithium hydroxide, cesium hydroxide, magnesium hydroxide, calcium hydroxide, sodium carbonate, potassium carbonate, cesium carbonate, sodium bicarbonate and potassium bicarbonate, or combinations thereof.

In accordance with an embodiment of the present invention, the base used in step (a) is sodium hydroxide.

In accordance with an embodiment of the present invention, the solvent used in step (a) is water.

In accordance with an embodiment of the present invention, in the step (a) of the process, the reaction is carried out at room temperature range of 20° C. to 35° C.

In accordance with an embodiment of the present invention, in the step (a) of the process the reaction is carried out at room temperature range of 20° C. to 35° C. for 2 h to 8 h.

In accordance with an embodiment of the present invention, in the step (b) of the process, the base used is selected from metal amide, metal hydride or metal ethoxide.

In accordance with an embodiment of the present invention, in the step (b) of the process, the base used is selected from sodium amide, potassium amide, lithium amide, sodium hydride or sodium ethoxide.

In accordance with an embodiment of the present invention, in the step (b) of the process, the base used is a metal amide.

In accordance with an embodiment of the present invention, in the step (b) of the process, the base used is sodium amide.

In accordance with an embodiment of the present invention, in the step (b) of the process, the reaction with base and solvent is carried out at a temperature maintained between 0° C. to 80° C.

In accordance with an embodiment of the present invention, in the step (b) of the process, the reaction with base and solvent temperature is carried out at a temperature maintained between 0° C. to 80° C. for 2 h to 6 h.

In accordance with an embodiment of the present invention, in the step (b) of the process, the reaction with base and solvent is followed by an acetic acid wash to remove dimer formed as impurity.

In accordance with an embodiment of the present invention, in the step (b) of the process, the acetylating agent is selected from acetyl chloride or acetic anhydride.

In accordance with an embodiment of the present invention, in the step (b) of the process, the acetylating agent is acetic anhydride.

In accordance with an embodiment of the present invention, in the step (b) of the process the acetylating agent is used in a catalytic amount from 0.05 equivalents to 0.5 equivalents.

In accordance with an embodiment of the present invention, in the step (b) of the process, the acetylating agent is used in a catalytic amount of 0.1 equivalent.

In accordance with an embodiment of the present invention, in the step (b) of the process, the reaction with acetylating agent is carried out at a temperature maintained from 0° C. to 50° C. for 2 h to 6 h.

In accordance with an embodiment of the present invention, in the step (b) of the process, the reaction with acetylating agent is carried out at a temperature maintained from 25° C. to 30° C. for 3 h to 4 h.

In accordance with an embodiment of the present invention, in the step (b) of the process, the reaction for preparation of the hydrochloride salt is carried out directly without isolation of verapamil as the free base.

In accordance with an embodiment of the present invention, in the step (b) of the process, the solvent is selected from a group consisting of dimethyl sulfoxide, toluene, hexane and acetonitrile or mixtures thereof.

In accordance with an embodiment of the present invention, in the step (b) of the process, the solvent used is toluene.

In the step (c) of the process, the said compound of formula V, obtained in step (b) is converted into the hydrochloride salt (the compound of formula I) by reacting it with hydrochloric acid in isopropyl alcohol (IPA) as per the method disclosed in U.S. Pat. No. 4,418,017.

The following examples which fully illustrate the practice of the preferred embodiments of the present invention are intended to be for illustrative purpose only and should not be considered in anyway to limit the scope of the present invention.

EXAMPLES

Step (a): Condensation of Compound of Formula II with Chlorobromopropane

In a round bottom flask, a solution of 101 g of sodium hydroxide (1.37 eq) flakes in 360 mL water was prepared and 360 g (1.0 eq) of 2-(3, 4-dimethoxyphenyl)-N-methylethanamine (NMVA, compound of formula II) was charged at 25-28° C. 7.2 g (0.012 eq) of Tetra butyl ammonium bromide (TBAB) was added followed by addition of 360 g of chlorobromopropane in 3 h at 25-28° C. The reaction mixture was stirred at 25-28° C. for 2 h and again was added 5.4 g (0.009 eq) of TBAB in 3 lots, maintaining the reaction mixture for 2 h at 25-28° C. after adding each lot. The reaction conversion was monitored by high performance liquid chromatography (HPLC). Once the NMVA content was observed to be less than 2.5%, 880 mL of water was added followed by 720 mL of toluene at the same temperature and the reaction mixture was stirred for 15 min. The organic layer was separated and the aqueous layer was again extracted with 200 mL of toluene. The combined organic layers were cooled to 10-15° C. Dilute hydrochloric acid (HCl) solution (415 g in 360 mL of demineralized (DM) water) was added at 10-15° C. The reaction mixture was washed with 2×360 mL toluene. 720 mL of fresh toluene was added to the aqueous layer and pH was adjusted to 12-13 using (250 g of Caustic dissolved in 250 mL of DM water) below 15° C. The reaction mixture was stirred for 15 min at 25-30° C., the organic layer was separated and aqueous layer was again extracted with 100 mL toluene. The combined organic layers were washed with 2×100 mL of water followed by 200 mL of brine solution. The organic layer was separated and distilled off (about 100 mL) to get the MC content below 0.3%. This toluene layer was directly proceeded with for next step without isolating the product, the compound of formula III. Alternatively, the product may be isolated.

Step (b): Preparation of Verapamil Base

In a clean and dry round bottom flask, was charged 625 mL of fresh toluene and 345 g (0.85 eq) of 2-(3,4-dimethoxyphenyl)-3-methylbutanenitrile (compound of formula IV) and stirred for 10 min at 25-30° C. 75 g (1.04 eq) of sodamide was added at same temperature. The reaction mixture was heated to 40° C. followed by addition of the toluene layer containing the compound of formula III slowly (temperature gradually increased to 65-70° C.). The reaction was heated to reflux temperature and maintained for 4 h. The reaction completion was monitored by HPLC. Once the content of the compound of formula III was found to be less than 1%, the reaction mixture was cooled to 30-35° C. 25 mL of methanol was added followed by 1800 mL of water and stirred for 20 min. The organic layer was separated and the aqueous layer was again extracted with 2×360 mL toluene. The combined organic layers were washed with 0.5% acetic acid solution 5-7 times (1.8 gm acetic acid in 360 ml demineralised water each time). The organic layer was checked for dimer impurity content by HPLC and washings were given till the dimer impurity content was found to be less than 0.3%. The organic layer was separated and 1-2 volumes of the solvent were distilled off to get a product with a moisture content (MC) less than 0.3%. 18.8 g (0.10 eq) of acetic anhydride was added to the reaction mixture and the reaction mixture was stirred for 3-4 h at 25-30° C. The reaction mixture was checked for desmethyl impurity content by HPLC (original content of 0.4-1.0% reduced to a limit NMT 0.1%). Water (720 mL) was added to the reaction mixture, which was stirred for 1 h, the pH was adjusted with 10% sodium bicarbonate solution to 7.0-7.5 (~1080 mL of 10% sodium bicarbonate solution). The organic layer was separated and washed with 360 mL of water. The organic layer was separated and distilled off by 1-2 volumes to get a product with a MC less than 0.3%. The toluene layer containing the product, the verapamil base represented as the compound of formula V was directly taken for next step (HCl salt formation). Alternatively, the product may be isolated.

Step (c): Preparation of Verapamil Hydrochloride

In a clean and dry round bottom flask, the organic layer of step (b) containing verapamil base was charged, 10 g of charcoal was added and the reaction mixture was stirred at 35-40° C. for 30 min. Charcoal was filtered and washed with 100 mL of toluene. The filtrate pH was adjusted to 3.0-3.5 with IPA. HCl (~17%) and stirred at 25-30° C. for 3 h. The reaction mixture was cooled to 0-5° C. and stirred for 1 h. The product was filtered and washed with 200 mL of toluene and the product was dried under vacuum at 50-55° C.

Yield: 670 g (74% for three steps); Purity by HPLC: 99.8% (No detection of desmethyl impurities and dimer impurity).

We claim:

1. A process for the preparation of verapamil hydrochloride represented as a compound of formula I,

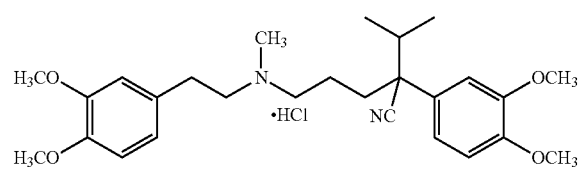

comprising the steps of:
  a) reacting compound of formula II

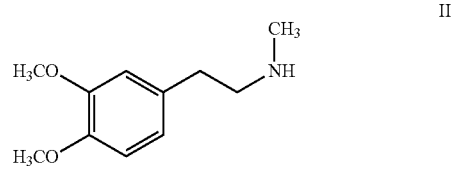

with chlorobromopropane, using a quaternary ammonium salt as a phase transfer catalyst in the presence of a base and a solvent to yield compound of formula III,

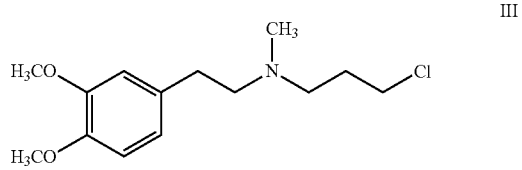 [SMILES: COc1ccc(CCN(C)CCCCl)cc1OC]

b) reacting the compound of formula III, obtained in step (a) with the compound of formula IV,

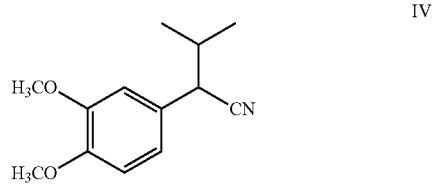

in the presence of a base and a solvent followed by reaction with an acetylating agent to yield compound of formula V, and

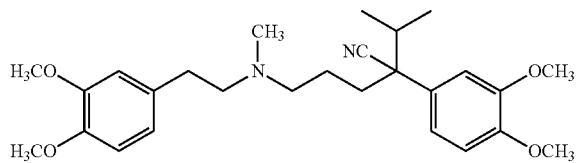

c) reacting the compound of formula V, obtained in step (b) using hydrochloric acid in isopropyl alcohol to prepare the corresponding hydrochloride salt represented as the compound of formula I

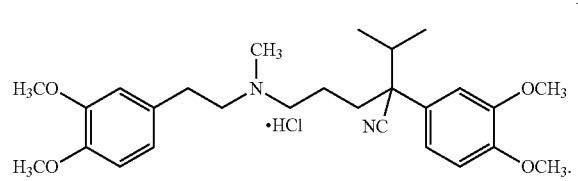

2. The process according to claim 1, wherein the quaternary ammonium salt phase transfer catalyst used in step (a) is selected from the group consisting of tricaprylyl methyl ammonium chloride (Aliquat 336), tetra-n-butylammonium bromide, benzyltriethylammonium chloride (TEBA), cetyltrimethylammonium bromide, cetylpyridinium bromide, N-benzylquininium chloride, tetra-n-butylammonium chloride, tetrabutylammonium bromide (TBAB), tetra-n-butylammonium hydroxide, tetra-n-butylammonium iodide, tetraethylammonium chloride, benzyltributylammonium chloride, hexadecyltriethylammonium chloride, tetramethylammonium chloride, hexadecyltrimethylammonium chloride, and octyltrimethylammonium chloride or combinations thereof.

3. The process according to claim 1, wherein the phase transfer catalyst used in step (a) of claim 1 is tetrabutylammonium bromide.

4. The process according to claim 1, wherein the base used in step (a) is an inorganic base selected from the group consisting of sodium hydroxide, potassium hydroxide, lithium hydroxide, cesium hydroxide, magnesium hydroxide, calcium hydroxide, sodium carbonate, potassium carbonate, cesium carbonate, sodium bicarbonate and potassium bicarbonate; or combinations thereof in a solvent.

5. The process according to claim 4, wherein the base used in step (a) of claim 1 is sodium hydroxide in water as solvent.

6. The process according to claim 1, wherein in step (a), the reaction is carried out at room temperature range of 20° C. to 35° C. for 2 h to 8 h.

7. The process according to claim 1, wherein in step (b), the base used is a metal amide.

8. The process according to claim 1, wherein in step (b), the base used is sodium amide.

9. The process according to claim 1, wherein in step (b), the reaction with base and solvent is carried out at a temperature maintained between 0° C. to 80° C. for 2 h to 6 h.

10. The process according to claim 1, wherein in step (b), the reaction with base and solvent is followed by an acetic acid wash to remove a dimer formed as impurity

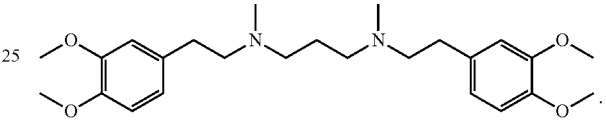

Dimer impurity

11. The process according to claim 1, wherein in step (b), the solvent used is toluene.

12. The process according to claim 1, wherein in step (b), the acetylating agent is selected from acetyl chloride or acetic anhydride.

13. The process according to claim 1, wherein in step (b), the acetylating agent is acetic anhydride used in a catalytic amount ranging from 0.05 equivalents to 0.5 equivalents.

14. The process according to claim 1, wherein in step (b), the reaction with acetylating agent is carried out at a temperature maintained from 0° C. to 50° C. for 2 h to 6 h.

15. The process according to claim 1, wherein the use of acetic anhydride acetylates the N-desmethyl and the O-desmethyl derivatives of verapamil obtained as impurities, which facilitates easy removal of these impurities due to selective crystallisation of verapamil hydrochloride resulting in a purity of the compound of formula I greater than 99%.

* * * * *